United States Patent [19]
Löfgrer et al.

[11] Patent Number: 4,674,655
[45] Date of Patent: Jun. 23, 1987

[54] VOLUME-VARIABLE CONTAINER FOR FLUIDS

[75] Inventors: Peter Löfgrer, Hovås; Nils Arthun, Partille, both of Sweden

[73] Assignee: Steridose Systems AB, Sweden

[21] Appl. No.: 800,296

[22] Filed: Nov. 21, 1985

[30] Foreign Application Priority Data

Nov. 23, 1984 [SE] Sweden .............................. 8405935
Mar. 20, 1985 [SE] Sweden .............................. 8501367

[51] Int. Cl.$^4$ .............................................. B65D 5/02
[52] U.S. Cl. .......................................... 222/48; 220/6;
222/103; 222/107; 222/214; 222/215; 229/41 R; 604/214
[58] Field of Search ................. 222/41, 44, 45, 47–50, 222/92, 95, 103, 105, 106, 107, 206, 215, 214, 209; 220/6; 229/41 R, 41 B, 7 R, 5.5; 383/121; 604/212, 214, 207, 246, 260, 262

[56] References Cited

U.S. PATENT DOCUMENTS

| | | | |
|---|---|---|---|
| 1,293,860 | 2/1919 | Mock | 222/92 |
| 2,718,983 | 9/1955 | Deskey | 222/92 |
| 3,418,059 | 12/1968 | Robe | 222/107 X |
| 3,648,895 | 3/1972 | Strazdins | 222/107 |
| 3,993,222 | 11/1976 | Briggs | 222/107 |
| 3,993,223 | 11/1976 | Welker, III et al. | 222/107 |
| 4,284,209 | 8/1981 | Barbour, Jr. | 222/48 X |
| 4,581,021 | 4/1986 | Landau et al. | 604/214 X |

*Primary Examiner*—Joseph J. Rolla
*Assistant Examiner*—Kevin P. Shaver
*Attorney, Agent, or Firm*—Wegner & Bretschneider

[57] ABSTRACT

A variable-volume container for fluids that is formed of a body portion and two end portions. The body portion comprises four rigid walls with each wall being joined to the next adjacent wall by a longitudinal fold line to permit collapsing of the container. The end portions of the container, each comprise, four sets of two triangular portions joined at fold lines to one another and to the walls of the body portion to permit the container to collapse without mechanical strain and substantial longitudinal motion of the end portions.

21 Claims, 24 Drawing Figures

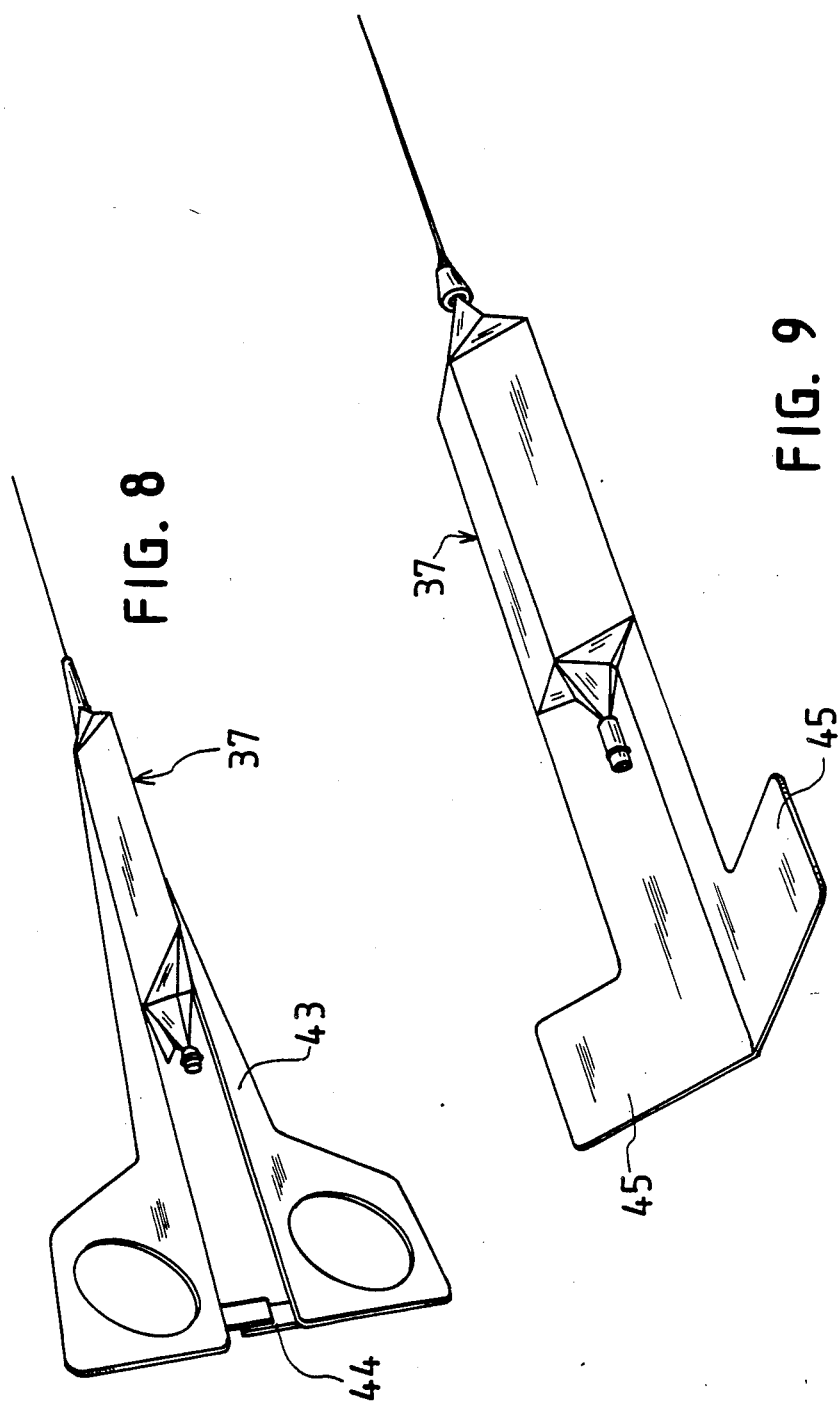

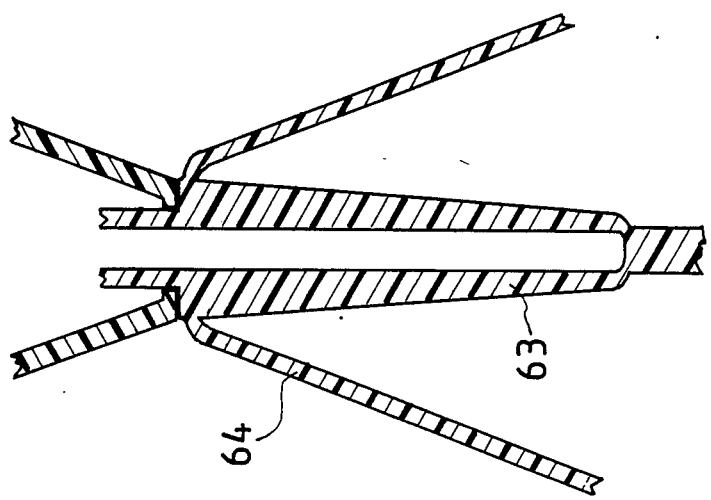
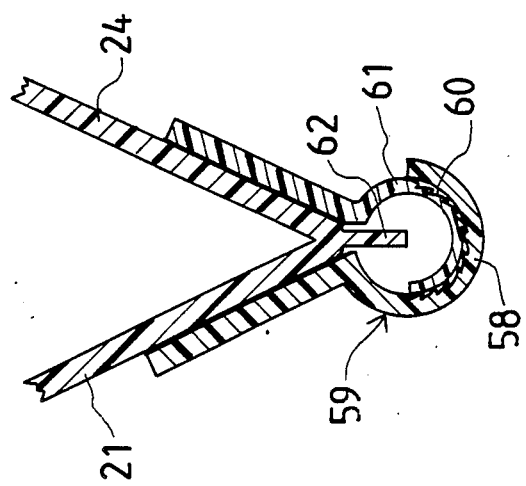

VOLUME-VARIABLE CONTAINER FOR FLUIDS

FIELD OF THE INVENTION

The present invention relates to a container of the type where the filling volume is dependent of the actual degree of erection of the container, i.e. basically a container having side walls which may be brought against each other and away from each other for defining a product accomodating space related to the degree of erection.

BACKGROUND OF THE INVENTION

The problem behind the invention is to provide a container at a reasonable cost level and of a type more or less universally useful and which, with a high degree of reliability, contains and discharges an exactly defined amount of a product. Differently stated it is thus necessary to realize a container structure that is emptiable to the last drip.

In case the container is to be used as the body of a syringe, which constitutes an important end use possibility, the problem is also to make the container ends stationary or with a minimum of movement in the longitudinal direction of the body when squeezing or pressing the container body. Such structure facilitates a proper handling of the syringe.

Additionally, the interior sides of the entire container structure should provide a structure that can be sterilized or made aseptic without troublesome operations and apparatuses and maintain the aseptic environment intact.

The handling of the container, especially in the syringe case, should be fault proof. The container should be able to manage fluids of varying viscosity.

Furtheron, the discharge of the product should be possible virtually regardless of the location of the region where a pressure is exerted onto the container for compressing the same and discharging the product.

As far as the filling is concerned it is of course necessary to know that the stipulated filling volume will be obtained. Although it is suitable to have a well defined filling volume built in in the container, in certain cases it will be possible to accept also a container structure where the filling volume primarily is defined by the filling equipment. This means that in certain applications it will be sufficient to have containers or packages which are filled only partly.

The problem according to the invention also involves the provision of a container basically designed to form the heart of a pump device for insertion in an arbitrarily chosen fluid system.

The pump device the invention primarily is concerned with, however, relates to a pump of the syringe type, especially a disposable syringe.

Thus, the problem according to the present invention also relates to the provision of a container structure of a type compatible with a sterile environment.

THE STATE OF THE ART

A large number of squeezable packages of a flexible or partially flexible type are previously known, for instance tubes of a great variety of different materials. As an example of materials it may be mentioned metal, plastic, cardboard and combinations of such materials. As far as the first mentioned category of tubes is concerned, the structure is such that a tube breast is arranged for making the tube form stable. Although there are various methods of making a tube breast completely compressible, for instance by using a small cone angle and by using local weakening denotations and/or grooves, it is still a problem to accomplish a complete emptying of the contents of the tube.

Provided the term partially flexible tubes also includes tubes having a bottom of the plunge type, the emptying degree possibly might be improved. However, still there is a breast portion which is difficult to handle.

OBJECTS OF THE INVENTION

The object of the present invention is to eliminate the drawbacks of known volume variable containers and offer a container which meets the stipulations according to the definition of the problem of the invention.

SUMMARY OF THE INVENTION

The invention provides a container for fluids, for instances liquids, comprising a container part having end closures at opposite ends thereof, a first set of folding denotations formed in the container part and extending parallel to an axis through centers of the end closures for defining a cross section perpendicular to said axis, along the entire length of the container part, comprising four sides, where at least pairs of sides are of the same length and the sides are interconnected along said first folding denotations for forming side walls of the container part, a second set of folding denotations defining sub panels in each end closure, said second folding denotations being geometrically placed such that the container part and the end closures are compressible to a plane state and expandable to a cross section where said cross section sides form an opening angle corresponding to a desired filling volume of the container, where said second set of folding denotations comprises denotations defining a first and a second triangular sub panel portion at the end of each side wall of the container part, and where each first triangular portion has a base that coincides with a cross section side and is of a length substantially equal to the length of the cross section side, and each second triangular portion forms at least part of a pointed extension of the container part.

The compressibility of the entire container structure to a planar state requires a placement of the second folding denotations in a geometrically correct position such that practically no mechanical strain appears in the structure when it is compressed or expanded. Additionally, and most important the geometrically correct placement also means end portions of the container that will not be displaced at all or will have a minimum displacement when compressing or expanding the container body.

In one embodiment of the invention two adjacent side walls of the container part and one set of first and second triangular portions, at each end of the container part, are formed as an integral unit having the appropriate number of said first and second folding denotations for forming a complete container by joining two such integral units.

The integral unit is symmetric relative one of said first folding denotations interconnecting adjacent side walls and one of said second folding denotations at each end of the unit, each one of said second folding denotations interconnecting two of said second triangular portions and defining the end of each pointed extension.

In order to obtain a geometrically correct positioning which is at an optimum, the placement of the first and second triangular portions preferably is such that adjacent pairs of first and second triangular portions have two points in common, one located on the symmetry line and the second close to the center line of the cross section side but somewhat displaced towards the symmetry line.

Two of said integral units are interconnected by means of pairs of skins, each extending circumferentially along a corresponding unit.

In one embodiment the side walls and sub panels of the end closures are interconnected by grooved folding denotations having substantially V-shaped cross section forming said first and second folding denotations.

In order to prevent deformation, for instance due to under pressure in the container, the side walls and the sub panels are rigid pressure resistant sections.

In thick plastic material, which for instance is injection moulded for forming said container units the folding denotations preferably have grooves of said substantially V-shaped cross section. In certain cases such grooves may also act as a latch against expansion and contraction from a certain predetermined position.

The grooves or whatever type of folding denotations that are used are always made in the outside of the container structure. This assures an interior surface, which is planar and suitable for aseptic or sterile applications.

In that case where the container should be placed in a pump system the container is provided with inlet and outlet connections arranged for connecting the container as a pump in a fluid system.

Said inlet and outlet connections may be formed in the pressure resistant side walls or in the end closures of the container.

In order to offer an aseptic or sterile environment directly when connecting the container to a fluid system or a needle, the inlet and outlet connections preferably are integral with tearable portions which provide a sterile surface between each portion and a respective connection surface of a hose or a needle.

In a preferable embodiment the container part and the end closures thereof are formed as an injection solution containing body of a syringe.

In order to facilitate the filling and the discharging procedure the container preferably is provided with means indicating actual container volume.

In one embodiment said means are integral with a device for squeezing the container part of the container.

In one embodiment, preferable from a production point of view, the container is manufactured of a material which is heat sealable at least along the sections of the container where the two integral units of the container are joined.

The material of the container, in one embodiment, is a plastic material having qualified gas barrier properties, for instance of the type ethylenevinylacetat (EVAL).

Specific accessories as a luer extension or pipette pipe may be arranged at the side walls or ends of the container part.

In one embodiment the volume indicating means comprises an elongated element of generally V-shaped cross section provided with means for attachment to the container part along the folding denotation between two adjacent side walls of the container part. A slot is formed in the V-shaped element and inside the slot there is a further element arranged for rotation around an axis extending in the direction of the slot and provided with a ramp having such a slope that the crossing point between the ramp and the margin of the slot represents the filling volume of the container part.

In one embodiment there is a positively acting latching device between adjacent side walls comprising a pair of elongated hook shaped dented elements arranged along said side walls for forming a snap type incremental latching device.

BRIEF DESCRIPTION OF THE DRAWINGS

FIG. 8 shows a container according to FIG. 7 used as a sryinge and provided with means for compressing the container, FIG. 9 shows an alternative embodiment of means for compressing, FIG. 21 shows a side wall locking device of incremental "snap type", FIG. 23 is a section through an encapsuled luer-extension.

DESCRIPTION OF PREFERRED EMBODIMENTS

Figure 1:
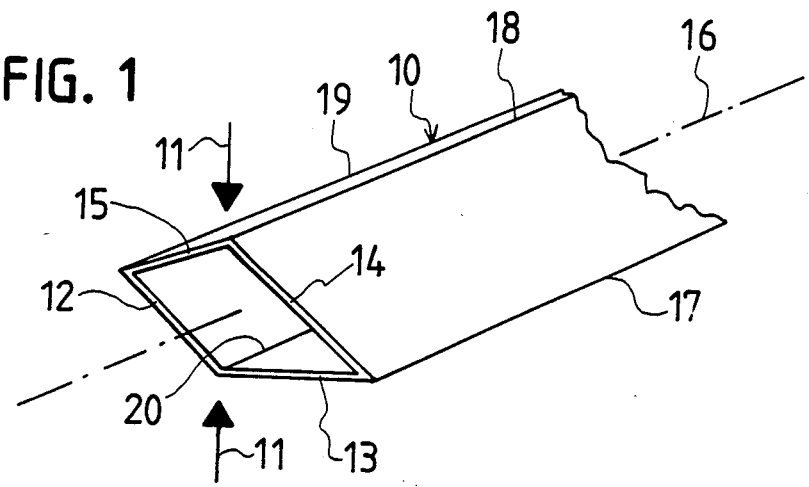
FIG. 1 shows a part of the container ready for compression.

The body 10 in FIG. 1 is that part according to one embodiment of the invention which forms the container part. The arrows 11 indicate a state where the cross section, formed by the cross section sides 12 to 15, is being compressed.

Figure 3:
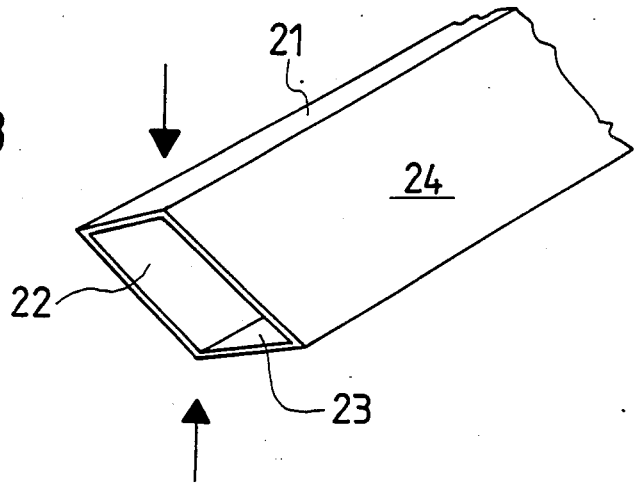
FIG. 3 shows a container part having a rhomboid (parallelogrammic) cross section.

The container part 10 in FIG. 1 has a center axis 16 which intersects the centers of the end closures (not shown in FIG. 1), one at each end of the container part. In FIG. 1 the cross section sides 12 to 15 are of the same length, but it is basically sufficient to have opposite pairs of sides of the same length, which the rhomboid embodiment in FIG. 3 shows.

Figure 2:
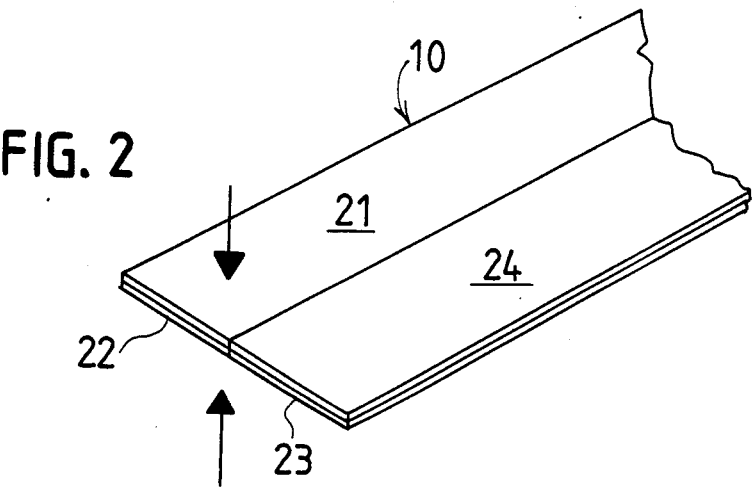
FIG. 2 shows the container in FIG. 1 in a compressed state.

The container part has a first set of folding denotations 17 to 20 arranged parallel to the center axis 16. Said folding denotations extend along the entire length of the container part, the whole way up to each end closure. This means that the side walls 21 to 24 of the container are completely compressible to the position according to FIG. 2.

The material of the container part 10 for instance is a thermoplastic material, such as a polyolefine, preferably polypropylene, which is a tough and durable hinge material.

However, different sorts of plastic laminates or sophisticated plastic qualities having qualified barrier characteristics may be used, depending on the gas barrier demands.

Figure 4:
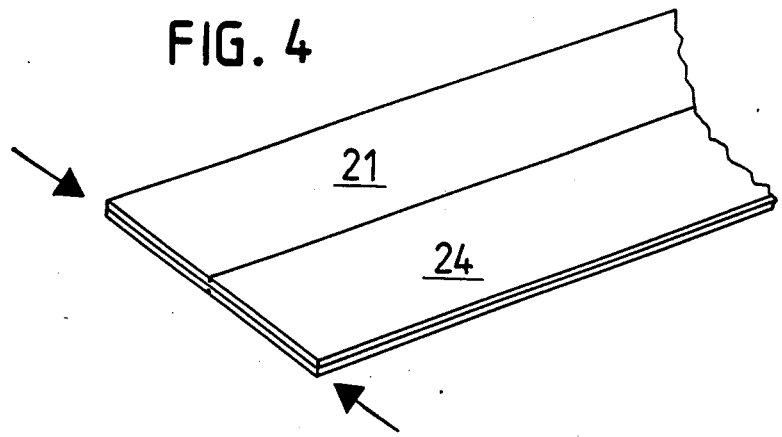
FIG. 4 shows the container part in FIG. 1 ready for being expanded.
Figure 5:
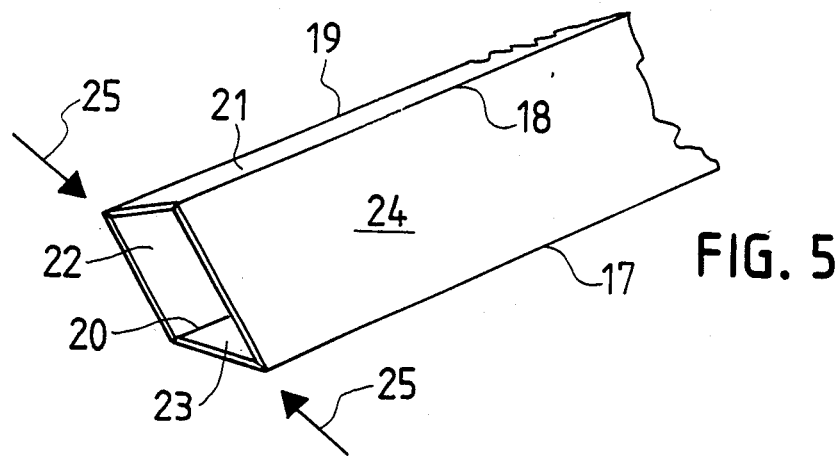
FIG. 5 is a perspective view from above and in front of the container part in an expanded state.

FIGS. 4 and 5 indicate that the expansion of the container part 10 is obtained by a force acting in the direction of the arrows 25, i.e. along the folding denotations 17 and 19.

Figure 6:
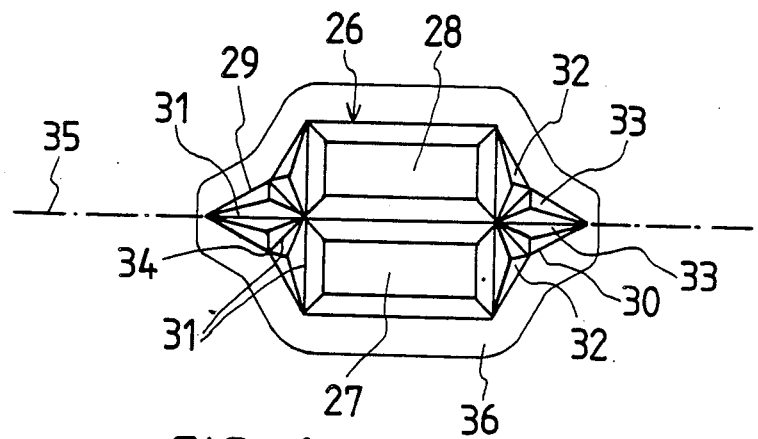
FIG. 6 is an end elevational view of an integral side wall and end closure unit for rational production of a complete container.

In FIG. 6 there is shown a practically useful embodiment of a integral unit 26 comprising a pair of side wall panels 27, 28 and end closure parts 29 and 30.

A folding denotation is shown between the side wall panels 27, 28. There is an extension of this folding denotation intersecting each end closure part in identical portions. A symmetry line of the unit 26 coincides with said folding denotations.

In the end closure parts 29 and 30 there are further folding denotations 31 belonging to a second set of folding denotations and delimiting sub panels 32, 33. Said panels are placed geometrically such that a container, formed by joining two units 26 along the circumference thereof, is compressible to a plane condition and expandable to a cross section corresponding to a desired container volume.

The expansion and compression, respectively, is obtained without creating any mechanical strain in the structure. The folding denotations, therefore, have been given an extension which may be called geometrically correct. Such strain free arrangements of folding denotations in the end closures also means that the end portions of the container closures will remain stationary or describe a minimum of longitudinal movement when compressing and expanding the container.

The sub panels 32 are shaped as first triangular panels or portions, each one having a base that coincides with a cross section side and of a length substantially equal to the length of the cross section side.

The sub panels 33 of the end closure are shaped as second triangular panels or portions, each one forming a pointed extension of each side wall 27, 28 of the container part. The geometrically correct placement of folding denotations, which will be defined more precisely in the following text, means that the pointed extensions will remain stationary when expanding and compressing the container.

In FIG. 6 two adjacent side walls 27, 28 of the container part and one set of first and second triangular portions 32 and 33, respectively, at each end of the container part blank in FIG. 6, are formed as an integral unit 26 having the appropriate number of said first and second folding denotations 17 to 20 and 31, respectively, for forming a complete container by joining two such integral units. In this specific embodiment the folding denotations are V-shaped grooves formed in a relatively thick, injection moulded plastics material. The thickness of the material is dimensioned such that it is pressure resistant. A force for compression expansion may be applied at any region of such container walls.

Each integral unit 26 is symmetric relative one of said first folding denotations interconnecting adjacent side walls 27, 28 and one of said second folding denotations 31 at each end of the unit. Each one of the second folding denotations 31 extending in the direction of the symmetry axis interconnects two of the second triangular portions 33 and defines the end of each pointed extension.

In order to obtain a geometrically correct structure which is at an optimum as far as minimum or no strain and stationary or almost stationary ends is concerned, adjacent pairs of first and second triangular portions 32, 33 have two points in common, one located on the symmetry line and the second 34 close to the center line of the cross section side but somewhat displaced towards the symmetry line.

In FIG. 6 there is also shown a peripherial circumferential flange 36. Portions of such flanges contribute to the folding denotation which is formed when identical units 26 are interconnected, preferably by welding, to a completed container.

Figure 7:
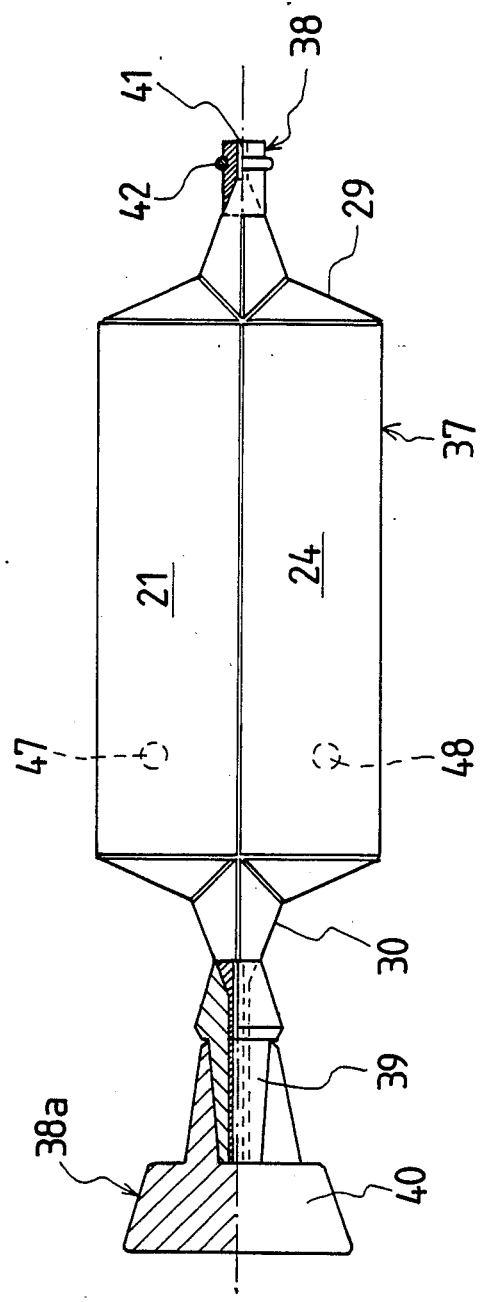
FIG. 7 shows a completed container having also a protecting device for sterile connection.

Such a completed container 37 is shown in FIG. 7. The end closures 29, 30 of this container have means 38, 38a protecting the connection regions for discharging or filling of the container alternatively for connecting it as a pump in a fluid system. Half of the portion 38 and half of the portion 38a are integral with the unit 26 in FIG. 6 and the interconnection to a completed means for protecting the connection regions occurs when two units 26 are interconnected. Alternatively, the connection parts 38, 39, 41 are manufactured separately and attached to the container when joining the two container halfs.

At the bottom in FIG. 7 there is shown a circumferential ledge 39 which is exposed when the grip portion 40 is teared off. The connection at the upper region of the container 37 in FIG. 7 has a needle guide 41 which is squeezed by a squeeze ring 42 in order not to be contaminated due to contact with the environment and which closes the container. Instead of having a squeeze ring it is possible to have a closure which is sealed for instance by welding.

The connections to external lines or other arrangements alternatively may be placed in a different place than at the end closures, especially when it is desirable to use the container 37 as a pump. The reference numerals 47, 48 show positions of connections in the relatively rigid side walls of the container.

In FIG. 8 the container 37 is an injection solution containing container for a syringe of disposable type. The container has a pair of squeeze and grip scissors 43, the legs of which are connected by a scale 44 indicating actual volume of the syringe body.

Another embodiment of a disposable syringe having a container according to the invention is shown in FIG. 9. The discharge of the contents of the syringe is obtained by pressing ears 45 away from each other.

Figure 10:
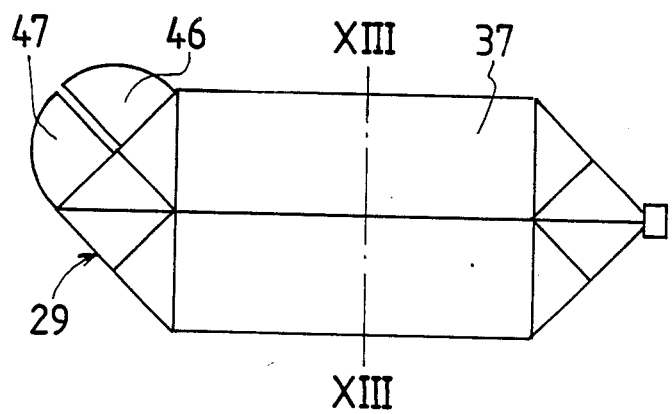
FIGS. 10 to 12 show a somewhat modified container structure in different expansion states.
Figure 11:
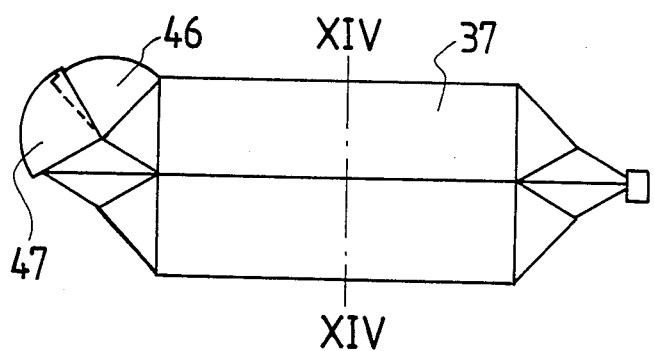
Figure 12:
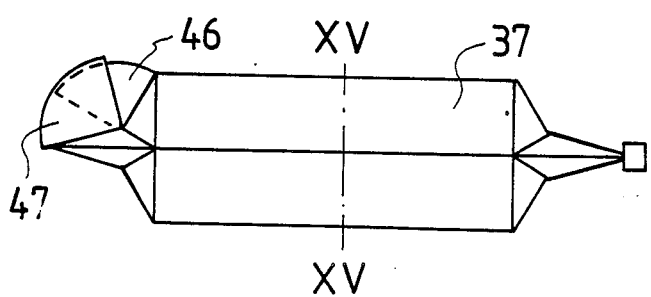
Figure 13:
FIGS. 13 to 15 are cross sections along lines XIII—XIII, XIV—XIV and XV—XV in FIGS. 10 to 12, FIGS. 16 to 18 show the basic container structure provided with a pipette arrangement.
Figure 14:
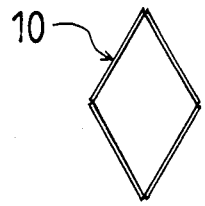
Figure 15:
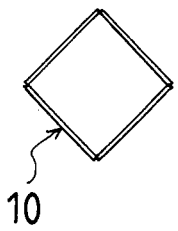

In FIGS. 10 to 12 there is shown a container body suitable for a disposable syringe and provided with extended portions 46, 47 on one end closure 29. Such extended portions 46, 47 are arranged to fall into each other following the expansion of the container body, as indicated in FIGS. 10 to 12 and 13 to 15, respectively. The extended portions indicate the actual filling degree (c.f. scale 44 in FIG. 8) and also act as a latch mechanism when necessary.

Figure 16:
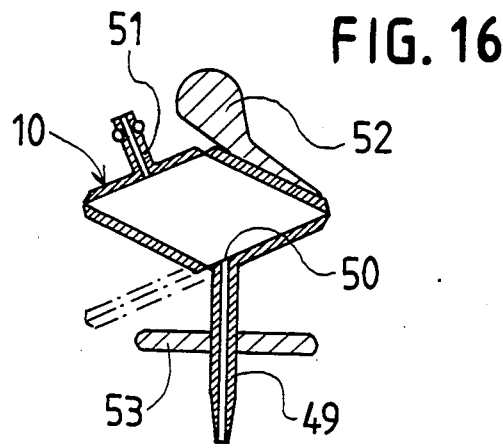
Figure 17:
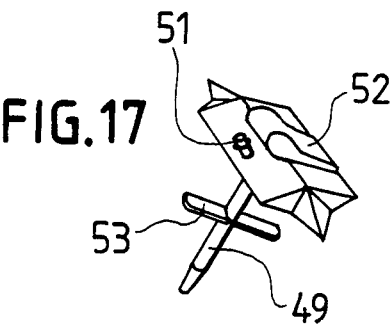
Figure 18:
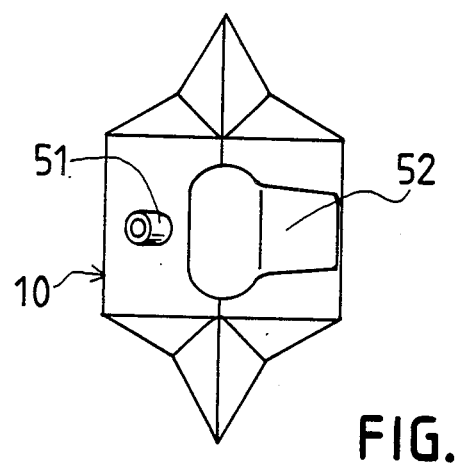

In FIGS. 16 to 18 there is shown the basic container structure according to the invention provided with details for forming for instance a pipette. A luer extension 49 is connected to an opening 50 in the container wall. In an opposite container wall there is arranged a filling channel 51 which possibly also may include a pressure element. In FIG. 16, however, a pressure element 52 is arranged on the adjacent container part wall.

On the luer extension 49 there is arranged a grip 53 which facilitates the handling of the device.

Figure 19:
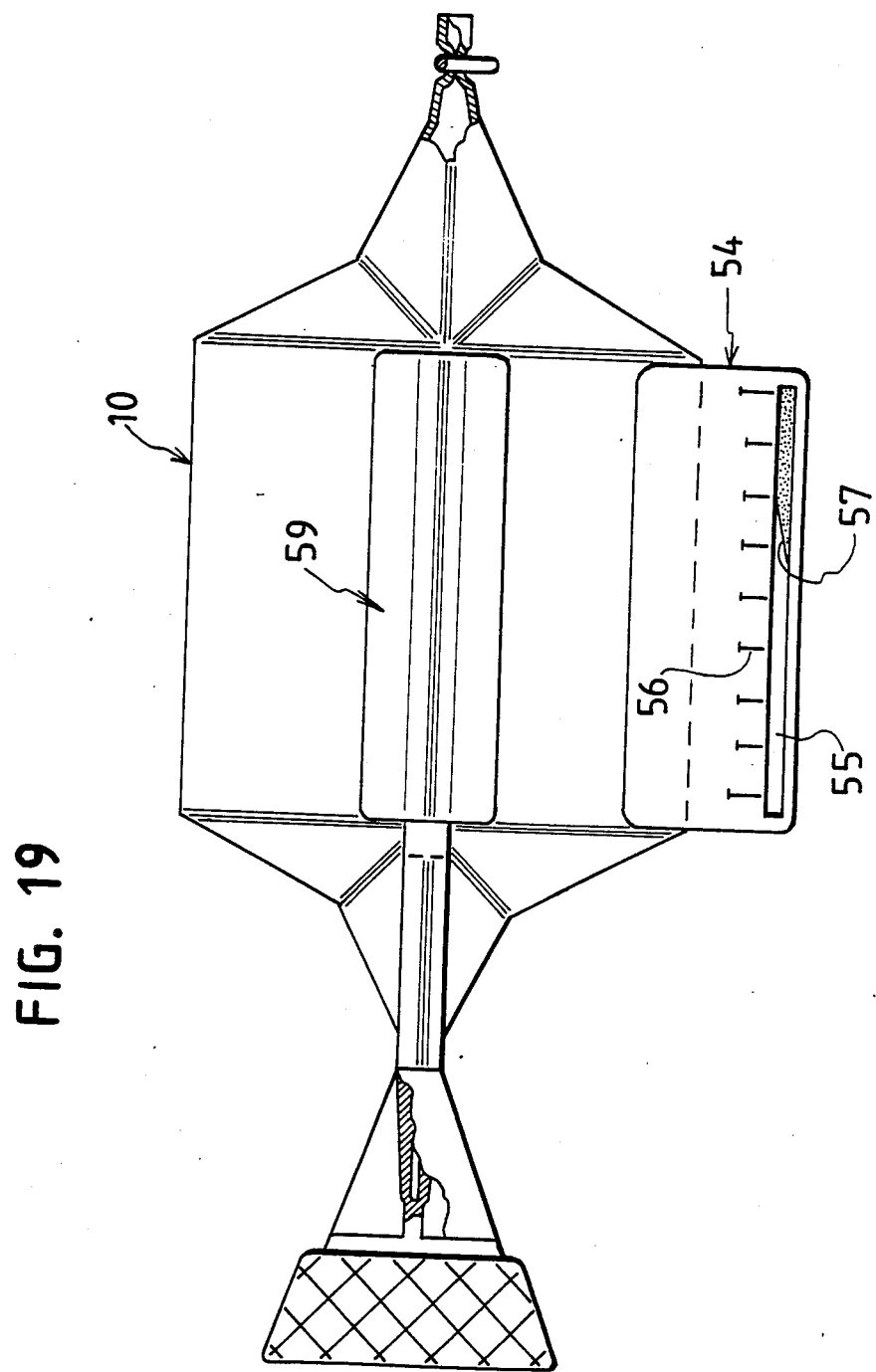
FIG. 19 shows a syringe having a volume indicator
Figure 20:
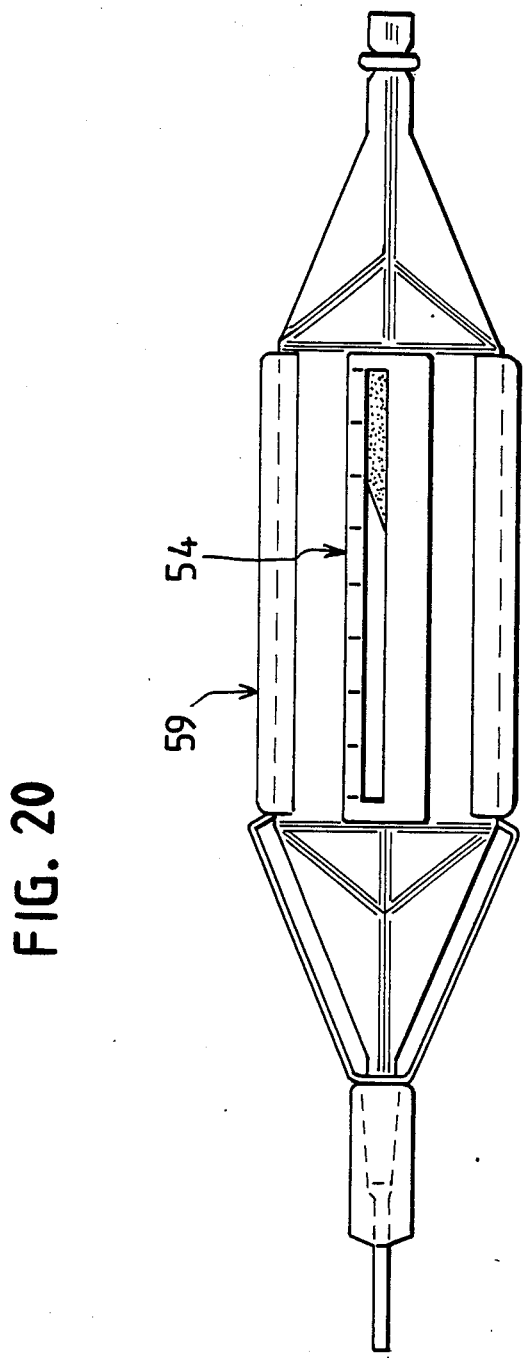
FIG. 20 shows the syringe in FIG. 19 in an elevation view perpendicular to the one in FIG. 19.
Figure 22:
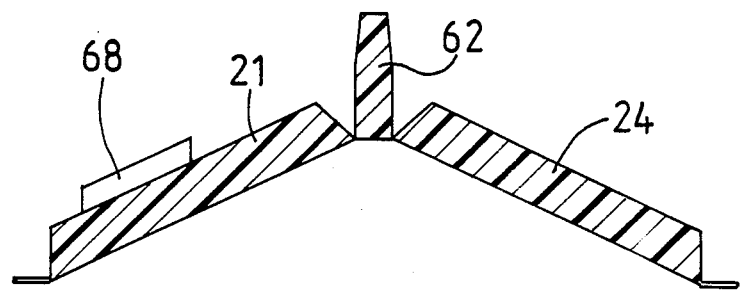
FIG. 22 represents a section through a pair of integral side walls of the container part of the syringe in FIGS. 19 to 21.

In FIGS. 19 to 21 the basic container structure is somewhat modified. An elongated element 54 of basically V-shaped cross section is snapped onto two adjacent walls of the container part of the syringe. A slot 55 is formed along the base of the V and is provided with indications or indicia 56 incrementally placed along the slot. Inside the slot there is an element basically arranged for rotation around an axis extending in the direction of the slot 55. The rotational movement of the element follows the opening degree of adjacent container part walls. On such an element there is printed a ramp 57 arranged with a slope such that the crossing point between the ramp and the margin of the slot represents the filling volume of the container body. Thus, the scale indicia directly represent actual filling volume.

The element having the ramp 57 printed thereon may for instance be the elongated hook 58 of the snap lock 59 in FIG. 21. There is a dented arrangement 60 between the hook 58 and a cooperating hook 61 providing an incremental locking function for adjacent walls 21, 24 of the container part of the syringe.

Figure 24:
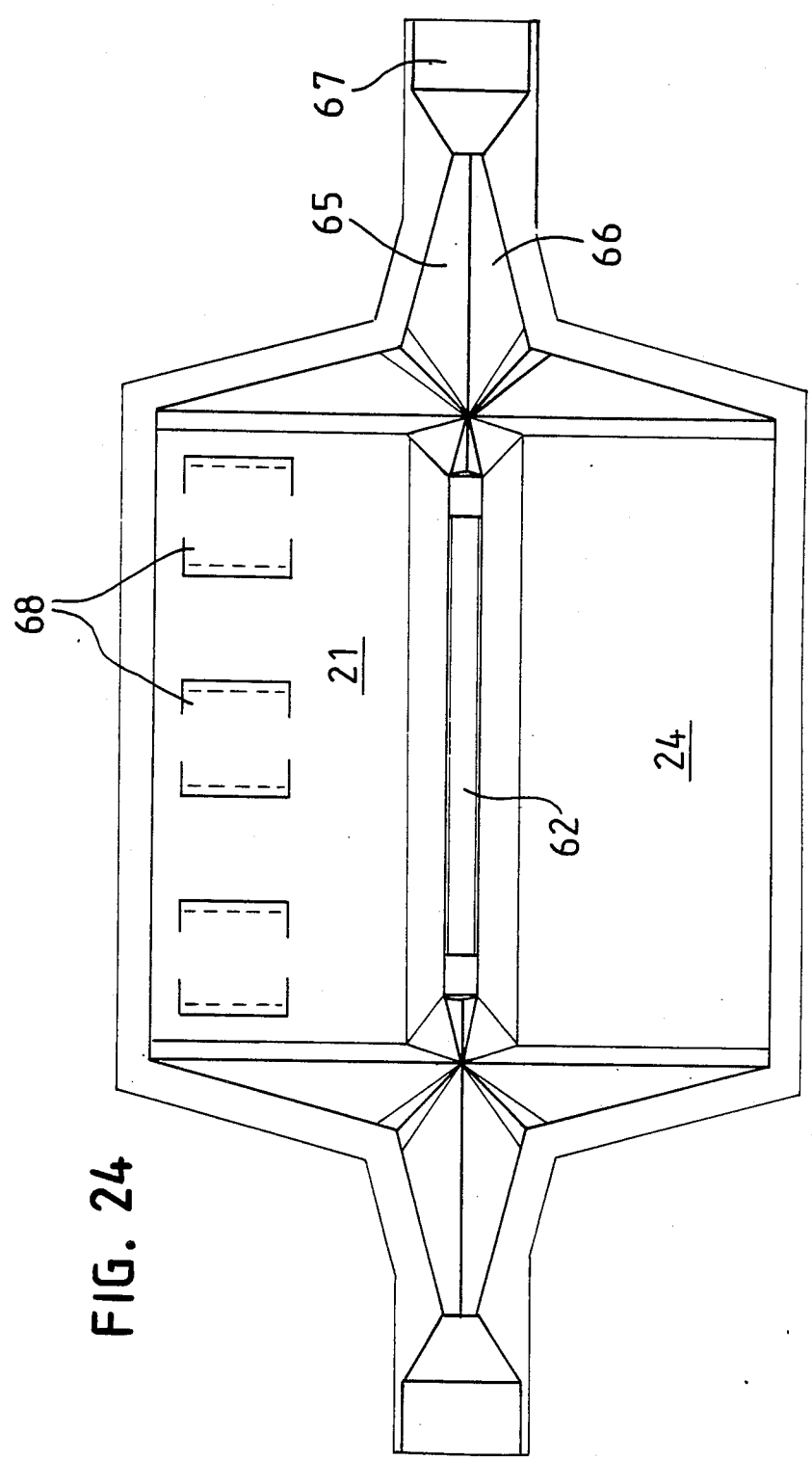
FIG. 24 is an elevation view showing a blank for forming half of syringe in FIGS. 19 and 20.

The arrangement for attaching the hook elements appears from FIG. 24. Dovetailed members 68 are formed on one side wall of each adjacent side wall pairs 21, 24. Such members 68 place and maintain the hook element 58 in the proper position. An elongated rib 62 prevents the element 58 from sliding downwardly in FIG. 21. The hook element 61 will be maintained in the correct position by the action of element 58.

In FIG. 23 a luer extension 63 is encapsuled within a circumferential wall 64 forming a barrier for maintaining a sterile environment at the luer extension.

The blank in FIG. 24 basically comprises the same set of first and second folding denotations as in FIGS. 6 and 7. For forming an encapsuled connection of the general type indicated in FIG. 23 each one of said second triangular portions 65, 66 integrally extends in the general direction of the pointed extension of the portions 65, 66 to form a semicircular recess 67. Such a recess forms half of the barrier housing of the luer extension.

We claim:

1. A dispensing apparatus for fluids which comprises a variable-volume container, said container comprising:
   (A) a body portion and an outwardly extending end portion at each end thereof;
   (B) said body portion comprising four rigid walls, each wall being joined to the next adjacent wall by a longitudinal fold line, said longitudinal fold lines being parallel to one another, said body portion being deformable between a first, collapsed position, and a second, open position wherein said container is deformable by the movement of two opposite pairs of adjacent walls away from each other during expansion and toward each other during compresion; and
   (C) said end portions each comprising four sets of two geometrically arranged triangular portions constituting means permitting the expansion and compression of said body portion without mechanical strain and substantial longitudinal motion of the end portions, said end portions each having a midpoint and four fold lines extending therefrom to each end of the longitudinal fold lines of said rigid walls, two of said fold lines lying along a line of symmetry, each set of two triangular portions having a first triangular portion having a base coterminous with the end of one of said walls, said base and said end of said wall joining along an edge fold line having first and second ends, and a second triangular portion having a base lying between said second end of the edge fold line and said midpoint along said line of symmetry, said first and second triangular portions having a common side at a common fold line, said common side extending from the second end of the edge fold line to one fold line of said other two fold lines at a point spaced between the first end of said edge fold line and said midpoint.

2. An apparatus as in claim 1, for use as a syringe, wherein the container includes a needle receiving portion connected thereto.

3. An apparatus as in claim 2, wherein the container includes volume indicating means, said volume indicating means being arranged along one of said longitudinal fold lines between adjacent walls of the body portion.

4. An apparatus as in claim 1, further including volume indicating means.

5. An apparatus as in claim 4, wherein the volume indicating means comprises a V-shaped device attached to the container along one of said longitudinal fold lines between two adajacent walls of the container body, said V-shaped device comprising two portions moveable relative to one another upon expansion and compression of the containers, one of said two portions having a slot with volume indicia disposed therealong and the other of said two portions being disposed behind said slot, said other portion having a volume indicator thereon which can be viewed through said slot.

6. An apparatus as in claim 4, further comprising means for compressing said container, said volume indicating means being integral therewith.

7. An apparatus as in claim 1, wherein the material of the container is formed of a substantially gas impermeable plastic material.

8. An apparatus as in claim 7, wherein the plastic material is ethyl vinyl acetate.

9. An apparatus as in claim 1, wherein the body portion includes an outlet having luer extension on one wall thereof.

10. An apparatus as in claim 9, wherein the wall opposite said one wall having said luer extension includes a filling means.

11. An apparatus as in claim 10, wherein a pressure means is arranged on said filling means.

12. An apparatus as in claim 10, wherein a pressure means is arranged on the wall adjacent to the wall having the luer extension.

13. An apparatus as in claim 1, wherein said pair of adjacent side walls of the body portion and two sets of said four sets of triangular portions, at each end of the body portion, are formed as an integral unit, whereby two of said integral units, when joined, form said container.

14. An apparatus as in claim 13, wherein each integral unit includes flange means extending cicumferentially about its edges to permit joining along a corresponding unit.

15. An apparatus as in claim 14, wherein said flange means are made of a heat sealable material.

16. An apparatus as in claim 14, wherein all of said fold lines comprise grooves having a substantially V-shaped cross-section.

17. An apparatus as in claim 16, wherein the triangular portions are rigid.

18. An apparatus as in claim 17, wherein the container includes inlet and outlet means.

19. An apparatus as in claim 18, wherein said inlet and outlet means are formed in the rigid walls of said body portion.

20. An apparatus as in claim 18, wherein said inlet and outlet means are formed in the end portions.

21. An apparatus as in claim 19 or 20, wherein the inlet and outlet means include tearable portions.

* * * * *

UNITED STATES PATENT AND TRADEMARK OFFICE
CERTIFICATE OF CORRECTION

PATENT NO.    :   4,674,655

DATED         :   June 23, 1987

INVENTOR(S)   :   Lofgren, Peter and Arthun, Nils

It is certified that error appears in the above-identified patent and that said Letters Patent is hereby corrected as shown below:

In the listing of inventors, change "Lofgrer" to --Löfgren--.

Signed and Sealed this

Third Day of November, 1987

Attest:

DONALD J. QUIGG

Attesting Officer

Commissioner of Patents and Trademarks